United States Patent [19]
Lichtenwalter et al.

[11] Patent Number: 5,910,410
[45] Date of Patent: *Jun. 8, 1999

[54] DUAL TAG BINDING ASSAY

[75] Inventors: Kay Lichtenwalter, San Jose; Calvin B. Ward, Castro Valley, both of Calif.

[73] Assignee: Hewlett-Packard Company, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/709,368

[22] Filed: Sep. 6, 1996

[51] Int. Cl.$^6$ ............................................. C12Q 1/68
[52] U.S. Cl. ................... 435/6; 435/6; 435/5; 435/4; 435/91.2; 435/7.17; 435/7.9; 436/56; 436/94; 436/501; 536/24.3; 536/24.33; 536/23.1
[58] Field of Search ................. 536/24.3–24.33, 536/23.1

[56] References Cited

U.S. PATENT DOCUMENTS

| | | | |
|---|---|---|---|
| 4,563,419 | 1/1986 | Ranki et al. | 435/6 |
| 5,521,065 | 5/1996 | Whiteley et al. | 435/6 |
| 5,565,322 | 10/1996 | Heller | 435/6 |
| 5,589,585 | 12/1996 | Mabilat et al. | 536/24.32 |

FOREIGN PATENT DOCUMENTS

| 2 283 569 | 5/1995 | United Kingdom | C12Q 1/68 |
|---|---|---|---|

*Primary Examiner*—Kenneth R. Horlick

[57] ABSTRACT

A method for detecting the presence of a target nucleic acid species having first, second and third target sequences. In the present invention, a solution to be tested is brought into contact with a solid support having a probe nucleic acid species attached thereto, the probe nucleic acid sequence comprising a sequence that is complementary to the first target sequence. A dye solution is then brought into contact with the solid support. The dye solution includes a first dye attachment nucleic acid sequence coupled to a first dye and a second dye attachment nucleic acid sequence coupled to a second dye. The first dye attachment nucleic acid sequence is complementary to the second target sequence and the second dye attachment nucleic acid sequence is complementary to the third target sequence. The ratio of concentrations of the first and second dye attachment nucleic acid sequences in the dye solution is different from the ratio of the first and second dye attachment sequences specifically bound by the target nucleic acid species. By measuring the ratio of the first and second dyes, non-specific binding of the dye attachment sequences can be detected. In one embodiment of the invention, the target nucleic acid sequence comprises a fourth target sequence, and the dye solution includes a third dye attachment nucleic acid sequence complementary to the fourth target sequence and coupled to a third dye.

3 Claims, 3 Drawing Sheets

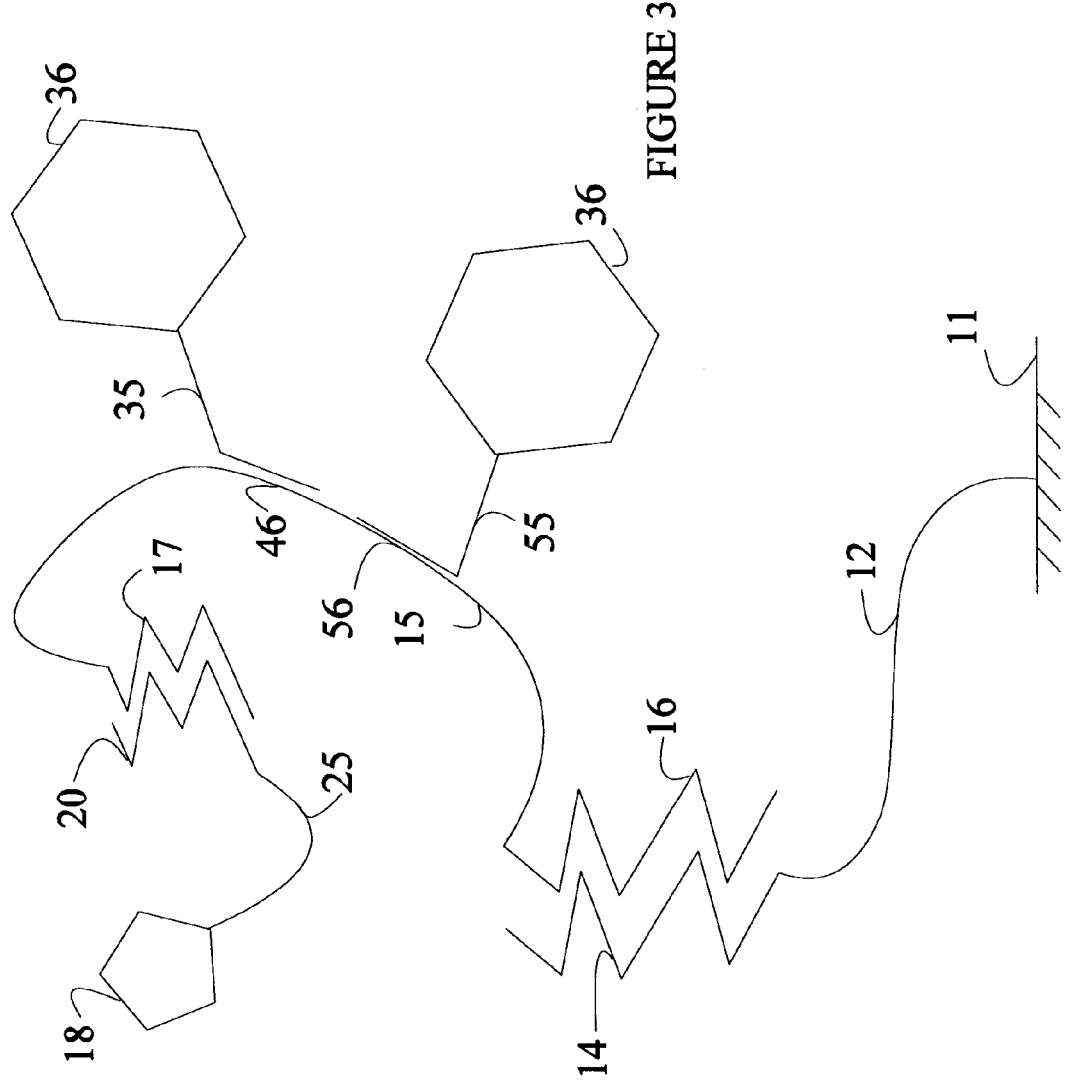

DUAL TAG BINDING ASSAY

FIELD OF THE INVENTION

The present invention relates to biochemical assays, and more particularly, to assays in which the presence of a target reactant is determined by measuring the amount of material that is bound to an immobilized reactant.

BACKGROUND OF THE INVENTION

Reactions between biological molecules exhibit an extremely high degree of specificity. It is this specificity that provides a living cell with the ability to carry out thousands of chemical reactions simultaneously in the same "vessel". In general, this specificity arises from the "fit" between two molecules having very complex surface topologies. For example, an antibody binds a molecule displaying an antigen on its surface because the antibody contains a pocket whose shape is the complement of a protruding area on the antigen. This type of specific binding between two molecules forms the basis of numerous biological assays.

For example, nucleic acids are linear polymers in which the linked monomers are chosen from a class of 4 possible sub-units. In addition to being capable of being linked together to form the polymers in question, each unit has a complementary sub-unit to which it can bind electrostatically. In the case of DNA, the polymers are constructed from four bases that are usually denoted by A, T, G, and C. The bases A and T are complementary to one another, and the bases G and C are complementary to one another. Consider two polymers that are aligned with one another. If the sequences in the polymers are such that an A in one chain is always matched to a T in the other chain and a C in one chain is always matched to a G in the other chain, then the two chains will be bound together by the electrostatic forces. Hence, an immobilized chain can be used to bind the complementary chain. This observation forms the basis of tests that detect the presence of DNA or RNA that is complementary to a known DNA or RNA chain. Such detection forms the basis of a number of medical and/or diagnostic tests.

The methods by which the binding of the mobile reactant to the immobilized component of the system is measured varies with the particular reactants. However, a significant fraction of all of the tests involve the measurement of a fluorescent dye that is associated with either the bound or mobile reactant. The dye may be attached to the reactant from the beginning of the process or it may be added through various chemical steps after the mobile and immobilized reactants have been brought into contact with one another.

The sensitivity of many assays is determined by the amount of non-specific binding that occurs between other macromolecules in the solution containing the mobile reactant and the substrate containing the bound reactant. The background material may bind to the substrate itself or to the bound reactant through binding reactions that are different from those for which the assay was designed.

The dye reactions utilized in prior art assay systems attach the dye molecule to a large class of macromolecules. For example, in antibody-antigen types of reactions in which the presence of antibody to a bound antigen is measured, the dye will be attached to any antibody that is bound to the substrate whether or not it is bound to the antigen. Similarly, in nucleic acid binding assays, the dye is bound to any double stranded region of nucleic acid. Hence, a mobile reactant that sticks to the surface of the assay plate and attracts its complementary strand is difficult to distinguish from a strand that is bound to the immobilized nucleic acid strand via the desired reaction. Similarly, a strand that binds by a partial sequence and is held in place by other binding reactions will also generate unwanted background.

Broadly, it is the object of the present invention to provide an improved binding assay.

It is a further object of the present invention to provide a binding assay that is less sensitive to non-specific binding than prior art binding reactions.

These and other objects of the present invention will become apparent to those skilled in the art from the following detailed description of the invention and the accompanying drawings.

SUMMARY OF THE INVENTION

The present invention is a method for detecting the presence of a target nucleic acid species having first, second and third target sequences. In the present invention, a solution to be tested is brought into contact with a solid support having a probe nucleic acid species attached thereto, the probe nucleic acid sequence comprising a sequence that is complementary to the first target sequence. A dye solution is then brought into contact with the solid support. The dye solution includes a first dye attachment nucleic acid sequence coupled to a first dye and a second dye attachment nucleic acid sequence coupled to a second dye. The first dye attachment nucleic acid sequence is complementary to the second target sequence and the second dye attachment nucleic acid sequence is complementary to the third target sequence. The ratio of concentrations of the first and second dye attachment nucleic acid sequences in the dye solution is different from the ratio of the first and second dye attachment sequences specifically bound by the target nucleic acid species. By measuring the ratio of the first and second dyes, non-specific binding of the dye attachment sequences can be detected. In one embodiment of the invention, the target nucleic acid sequence comprises a fourth target sequence, and the dye solution includes a third dye attachment nucleic acid sequence complementary to the fourth target sequence and coupled to a third dye.

BRIEF DESCRIPTION OF THE DRAWINGS

FIG. 3 illustrates the manner in which a binding assay for measuring the number of target molecules carrying a specific sequence is carried out when multiple dye nucleic sequences are utilized.

DETAILED DESCRIPTION OF THE INVENTION

To simplify the following discussion, the present invention will be described with reference to assays for nucleic acids, either RNA or DNA. Such assays are based on nucleic acid hybridization reactions in which the presence of nucleic acids having a specific sequence in a soluble fraction is determined by measuring the amount of nucleic acid bound to a surface having a sequence complementary to at least a portion of the desired sequence immobilized thereon.

Figure 1:
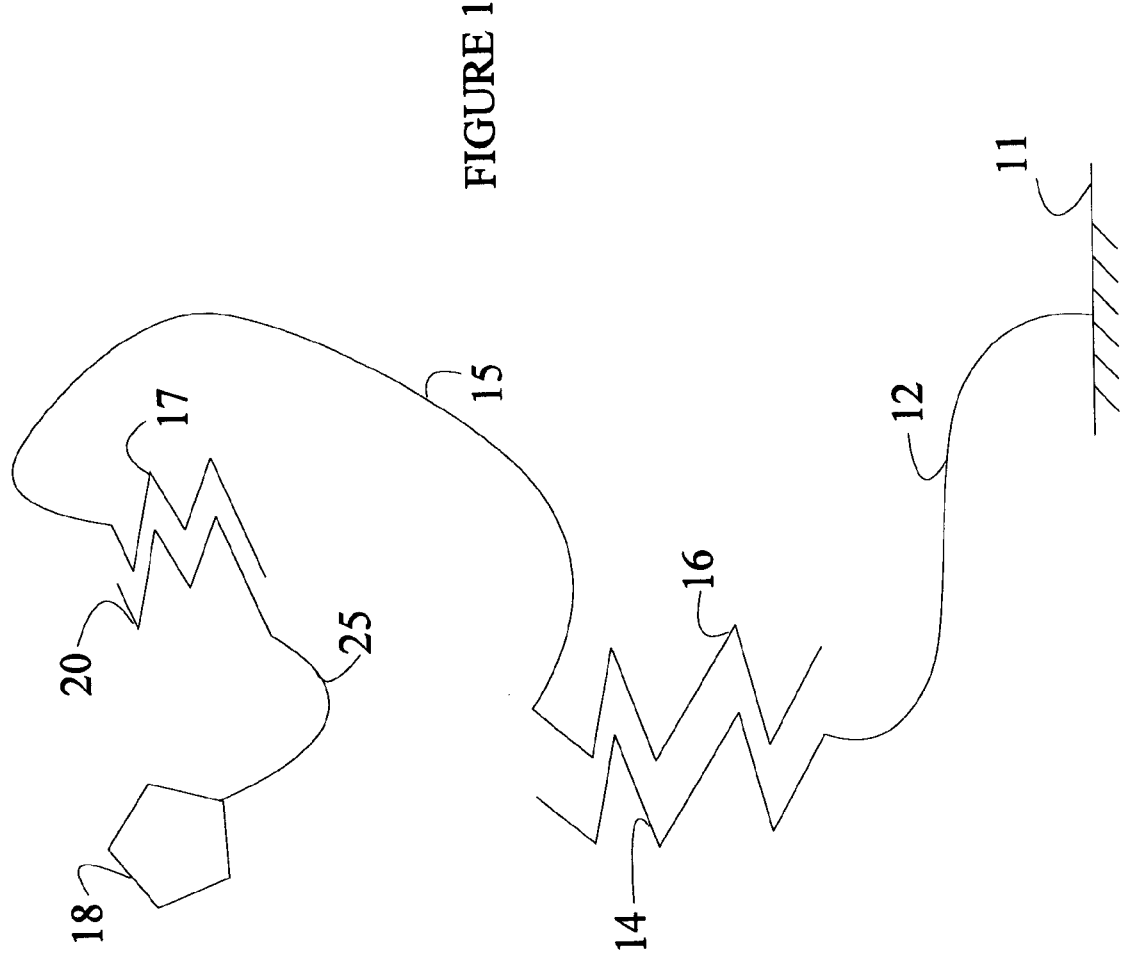
FIG. 1 illustrates the manner in which a binding assay for measuring the number of target molecules carrying a specific sequence is carried out.

The present invention may be more easily understood with reference to a prior art assay in which the dye molecule used to detect a bound target molecule is itself linked to a nucleic acid sequence. Refer now to FIG. 1 which illustrates the manner in which a binding assay for measuring the number of target molecules 15 carrying a specific sequence is carried out. The specific sequence which is to be measured is divided into two sites 16 and 17. The sites may be adjacent to one another, or they may be separated by some distance on the target molecule 15. The later case is shown in FIG. 1. The target molecule 15 binds an immobilized species 12 in a first location 16 on the target molecule via a complementary sequence 14 on immobilized species 12. A second site 17 on the target molecule is used to bind the detection dye 18 which is bonded to a complementary attachment site 20 on a third sequence 25 which will be referred to as the "dye" nucleic acid sequence. This second attachment reaction must be more selective for the target species being sought than for the background materials that non-specifically attach to immobilized species 15 or support 11 for this type of assay to function.

Figure 2:
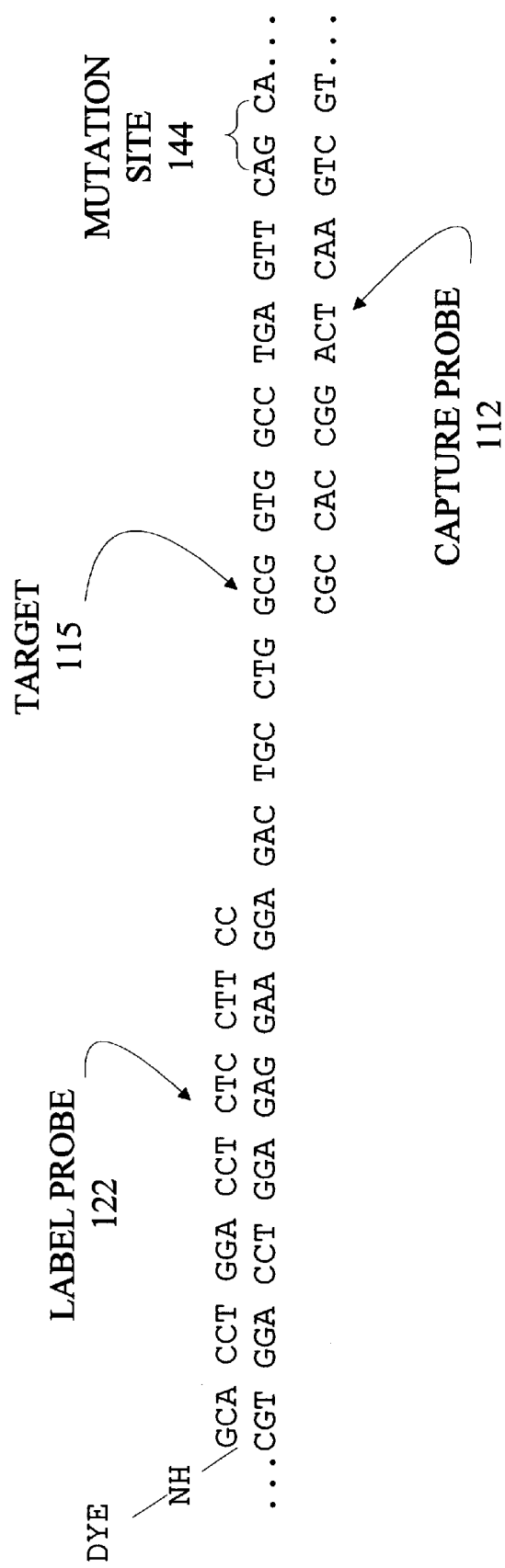
FIG. 2 illustrates the DNA sequences used in one embodiment of the present invention.

This type of assay may be more easily understood with reference to a specific assay for detecting the presence of a mutation leading to one form of Diabetes. The various DNA sequences used to construct the assay are shown in FIG. 2. The capture probe 112 (SEQ ID NO 3) is designed to bind to the area around the mutation site 144 on the target DNA 115 (SEQ ID NO 2). The dye is carried on a label probe 122 which binds to another portion of the target 115. In this example, the dye is connected to the probe sequence via an amino group at the 3' end of the probe sequence.

The dye is preferably attached to the probe DNA sequence via an amino group in a synthetic oligonucleotide sequence. The amino group can be at either end of the sequence or on a nucleotide within the sequence. The choice of dye and binding reaction are a matter of design choice. Labeling of oligonucleotide sequences with suitable dyes is well known to those skilled in the DNA hybridization arts, and hence will not be discussed in detail here.

The preferred dye is Cy5 which is a member of the sulfoindocyanine family of dyes. These dyes are preferred because they produce less autoflourescense compared to other suitable dyes. The Cy5 dye may be obtained commercially from Amersham Life Science, Inc. of S. Arlington Heights, Ill. The dye is bound to the amino group of the modified target sequence as follows: 30 nanomoles of 5' end amino modified oligonucleotide in 0.5 ml of 1×TES buffer (0.1 M TES, 0.15 M NaCl, 1 mMEDTA, pH 7.5) is added to 80 nanomoles of Cy5 dye and mixed thoroughly. The reaction is incubated at room temperature for 15 minutes to 1 hour with additional mixing at 5–10 minute intervals. The labeled oligonucleotide is separated from the free dye using gel filtration. A Bio-Gel P-4 column of approximately 10 cm length and 8 mm diameter satisfactorily separates the material. Absorbency at both 260 and 656 nm may be used to confirm labeling of the oligonucleotide.

The above described prior art embodiments have utilized a single dye sequence. These embodiments cannot easily distinguish between dye sequences that are properly bound to the immobilized target and sequences that bind non-specifically to the surface on which the target is immobilized. The present invention provides a method for detecting such non-specific binding. Refer now to FIG. 3 which illustrates a detection system in which two or more dye sequences are utilized. The first dye sequence is the same as that described above with respect to FIG. 1; hence, the sequences and dyes are labeled with the same designations. A second dye sequence 35 and perhaps a third dye sequence 55 which are complementary to the target species at a location 46 and 56 are also used. Dye sequence 35 includes a dye 36 which may be the same or different from dye 18. If the same dye is used, the additional dye sequence merely enhances the signal from the bound target. Since it is assumed that the dye sequences at least have a greater affinity for the target than the surrounding materials, this enhancement provides an improvement over the prior art.

However, in the preferred embodiment of the present invention, a different dye is used on the second dye sequence. For example, dye 18 can be the Cy5 dye described above which is detected at 667 nm, and dye 36 can be Cy3 which belongs to the same family of dyes, but which is detected at 565 nm. The ratio of the fluorescence at the two detection wavelengths may be used to provide quality control for an assay based on nucleic acid hybridization. If either dye sequence is non-specifically bound to other structures in the assay plate, the ratio of the observed fluorescence will be different from that predicted for specific attachment. The two dye molecules may be detected separately by using dyes that emit light at different wavelengths when excited or by using dyes that are excited at different wavelengths.

In the following discussion, it will be assumed that any non-specific binding of the dyes or dye sequences to the support is related to the concentration of the binding species. If there are a fixed number of sites on the support at which any sequence can bind in a non-specific manner, the first and second dye attachment species will compete for these sites, and hence, the amount of each that is bound will depend on the relative concentrations of the dye attachment species in the dye solution.

The extent to which the background binding is interfering with the assay for the target species may be determined in a number of ways if two dyes are used. To simplify the following discussion, it will be assumed that the dyes have equal detection efficiencies. That is, one molecule of the first dye generates the same number of photons in the assay at the first dye's detection wavelength as one molecule of the second dye generates at the second dye's detection wavelength. Hence, the ratio of the fluorescence at the first and second dye detection wavelengths will be 1:1 for the portion of the dye that is specifically bound to the target sequences by the dye attachment sequences independent of the concentration of the dye attachment sequences in the dye solution. Here, it is assumed that the dye attachment sequences are present in sufficient concentrations to saturate the available sites on the target sequence.

As noted above, the non-specifically bound dye sequences are expected to appear in a ratio determined by their respective concentrations in the dye solution. Non-specific binding can be detected by comparing the measurements obtained with a dye solution having a different ratio of concentrations than that predicted for the specifically bound dye sequences. For example, if the dye solution contains a 2:1 concentration of the first and second dye attachment sequences, then the non-specifically bound dye would contribute a signal that is weighted by 2:1 in favor of the first dye. Similarly, a dye solution containing a 1:2 ratio of the first and second dye attachment sequences will generate a background that is weighted by 1:2 in favor of the second dye. If there are equal numbers of sites on the target, the target will contribute a signal in which the ratio of the fluorescence at the two wavelengths is 1:1. Hence, a measured ratio that differs from 1:1 significantly indicates a significant amount of non-specific binding. In general, by using a dye solution that contains a significantly different ratio of concentrations of the dye attachment sequences than the ratio of concentrations of these sequences that bind to the target, non-specific attachment can be detected.

The ratio of the dyes that are specifically bound depends on the number of dye attachment sequences used on the target sequence. As noted above, additional sites may be used on the target sequence. Consider the case in which the target sequence binds three dye sequences, one with the first dye and two with the second dye. Then the expected fluorescence ratio from the specific binding is 1:2 in favor of the second dye. If equal concentrations of the first and second dyes are present in the dye solution, the background will contribute a signal with a ratio of 1:1 for the fluorescent measurements at the two wavelengths. In general, a ratio of 1:X will be observed where X is between 1 and 2. The extent to which X is different from 2 is a measure of the non-specific binding, and hence, may be used as a quality control in the assay. Hence, a third dye attachment site can be used to enhance the background detection.

Various modifications to the present invention will become apparent to those skilled in the art from the foregoing description and accompanying drawings. Accordingly, the present invention is to be limited solely by the scope of the following claims.

bringing a solution to be tested in contact with a solid support having a probe nucleic acid sequence attached thereto, said probe nucleic acid sequence comprising a sequence that is complementary to said first target sequence; and bringing a solution including a dye solution in contact with said solid support, said dye solution comprising a first dye attachment nucleic acid sequence coupled to a first dye and a second dye attachment nucleic acid sequence coupled to a second dye, said first dye attachment nucleic acid sequence being complementary to said second target sequence and said second dye attachment nucleic acid sequence being complementary to said third target sequence, said first dye having a different emission spectrum than that of said second dye, said solution including said dye solution providing conditions enabling said first and second dye attachment nucleic acid sequences to hybridize to said second and third target sequences, respectively, thereby binding said first and second dye attachment nucleic acid sequences to said solid support via said probe nucleic

What is claimed is:

1. A method for detecting the presence of target nucleic acid molecules having first, second and third target sequences, said method comprising the steps of:

acid sequence; and measuring the quantities of said first and second dyes bound to said solid support.

2. The method of claim 1 wherein the ratio of concentrations of said first and second dye attachment nucleic acid sequences in said dye solution is different from the ratio of said first and second dye attachment sequences specifically bound by said target nucleic acid molecules.

3. The method of claim 1 wherein said target nucleic acid molecules comprises a fourth target sequence and wherein said dye solution comprises a third dye attachment nucleic acid sequence coupled to a third dye, said third dye attachment nucleic acid sequence being complementary to said fourth target sequence.

* * * * *

```
                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH:20 base pairs
        (B) TYPE: nucleic acid
        (C) STRANDEDNESS: Single stranded
        (D) TOPOLOGY: linear (xi) SEQUENCE DESCRIPTION: SEQ ID NO:1:

CCTTCCTCTC  CAGGTCCACG                                              20

(2) INFORMATION FOR SEQ ID NO:2:

(i) SEQUENCE CHARACTERISTICS:
        (A) LENGTH:50 base pairs
        (B) TYPE: nucleic acid
        (C) STRANDEDNESS: Single stranded
        (D) TOPOLOGY: linear (xi) SEQUENCE DESCRIPTION: SEQ ID NO:2:

CGTGGACCTG  GAGAGGAAGG  AGACTGCCTG  GCGGTGGCCT  GAGTTCAGCA          50

(2) INFORMATION FOR SEQ ID NO:3:

(i) SEQUENCE CHARACTERISTICS:
        (A) LENGTH:20 base pairs
        (B) TYPE:nucleic acid
        (C) STRANDEDNESS:Single stranded
        (D) TOPOLOGY: linear (xi) SEQUENCE DESCRIPTION: SEQ ID NO:3:

TGCTGAACTC  AGGCCACCGC                                              20
```